(12) United States Patent
Ring et al.

(10) Patent No.: US 6,397,879 B1
(45) Date of Patent: Jun. 4, 2002

(54) IN-LINE FLUID TREATMENT DEVICE

(76) Inventors: Russ Ring, 5950 W. Branch Rd.; Morrison Richard, 6650 Woodedge Rd., both of Minnetrista, MN (US) 55364

( * ) Notice: Subject to any disclaimer, the term of this patent is extended or adjusted under 35 U.S.C. 154(b) by 0 days.

(21) Appl. No.: 09/760,134

(22) Filed: Jan. 12, 2001

(51) Int. Cl.⁷ .................................................. B01F 1/00
(52) U.S. Cl. ..................... 137/268; 422/264; 4/226.1
(58) Field of Search ............................. 137/268; 4/224, 4/226.1; 422/264, 261

(56) References Cited

U.S. PATENT DOCUMENTS

| | | | |
|---|---|---|---|
| 3,443,590 A | * | 5/1969 | Wagner et al. .......... 137/268 X |
| 5,404,594 A | * | 4/1995 | Ring et al. .............. 137/268 X |
| 5,810,043 A | * | 9/1998 | Grenier ...................... 137/268 |
| 5,927,610 A | * | 7/1999 | Dutcher .................. 137/268 X |

* cited by examiner

Primary Examiner—Kevin Lee
(74) Attorney, Agent, or Firm—Merchant & Gould P.C.

(57) ABSTRACT

A fluid treatment device adapted to be disposed in-line with a fluid flow path, particularly suited for use as an in-line toilet cleaner. The device is suitable for use with fluid pressures of at least 500 pounds per square inch. The device includes inlet and outlet ports for connection to a fluid supply and a fluid exhaust. The device has a fluid treatment chamber for use with a replaceable fluid treatment cartridge inserted therein. The fluid treatment cartridge may be a chemical compound such as a detergent, or a mechanical or electrical treatment device. The device also includes a valve mechanism for controlling the portion of fluid that passes through the treatment chamber before exiting the device, and an adjusting knob for manipulating the valve position. The device has a pressure release valve. The device may include an indicator for indicating when the treatment cartridge must be replaced.

20 Claims, 4 Drawing Sheets

IN-LINE FLUID TREATMENT DEVICE

BACKGROUND OF THE INVENTION

The present invention relates to a fluid treatment device adapted to be disposed in-line with the path of fluid flow. The present invention is in particular suitable for use as an in-line cleaning device for a toilet bowl.

Currently, there are many devices available for treating fluid. In-line fluid treatment devices, which are adapted to be connected to a fluid supply and a fluid exhaust, whereby all the fluid from the supply must pass through the fluid treatment device to reach the exhaust, are known. In-line fluid treatment devices are advantageous, in that they permit treatment of all the fluid flowing through a particular supply. In addition, although in-line devices may be attached to secondary fluid lines or devices, they may also be installed on the primary fluid line, permitting relatively simple installation and maintenance tends to be simpler.

In-line fluid treatment devices are particularly suitable for use as, for example, in-line toilet bowl cleaners. One example of such a device is shown in U.S. Pat. No. 5,404,594.

However, current in-line fluid treatment devices suffer from several limitations. For example, known devices tend to leak if subjected to high internal pressures. Because the fluid pressure inside an in-line fluid treatment device is typically equal to the pressure in the fluid supply and the fluid exhaust, this limits the pressure that may be used in any system directly connected to such a device.

In addition, known in-line fluid treatment devices are prone to uneven treatment, in particular due to poor internal fluid circulation. This limits their utility in cases where fluid must be uniformly treated.

The present invention provides an improved in-line fluid treatment device which solves many of the above noted problems.

SUMMARY OF THE INVENTION

The present invention relates to an in-line fluid treatment device. The in-line fluid treatment device is suitable for connection with a fluid supply and a fluid exhaust.

This application hereby incorporates by reference the disclosure of U.S. Pat. No. 5,404,594. In particular, it is noted that the exemplary valve structure illustrated and described therein would also be suitable for use with a device in accordance with the principles of the present invention.

One embodiment of an in-line fluid treatment device in accordance with the principles of the present invention includes a housing with a base and a cover, the base and covers engaging to form a fluid-tight fit. The base and cover cooperate to define a treatment chamber within the housing. The embodiment also comprises a retainer for removably retaining the cover on the base. A treatment cartridge is disposed within the treatment chamber, the treatment cartridge being adapted to treat fluid passing through the treatment device. The embodiment further comprises an in-line conduit for conducting fluid from the fluid supply to the treatment chamber, and thence to the exhaust, and likewise for conducting fluid from the fluid supply directly to the fluid exhaust. The embodiment also comprises a valve for controlling the flow of fluid through the in-line conduit, and an adjusting mechanism for adjusting the valve, so as to control the portion of fluid from the fluid supply that flows to the treatment chamber.

In another embodiment of an in-line fluid treatment device in accordance with the principles of the present invention, the treatment device is suitable for use with fluid supply pressures of at least 500 pounds per square inch.

In yet another embodiment of an in-line fluid treatment device in accordance with the principles of the present invention, one of the base and cover has a generally annular lip, and the other has a generally circular opening, wherein the lip is sized so as to fit in the opening so as to form a fluid-tight fit when the base and cover are engaged. In this embodiment, when pressure inside the housing exceeds pressure outside the housing, the pressure differential biases the lip outward, against the edge of the opening. Thus, as pressure increases, any deformation of the housing results in a tighter seal, rather than in the formation of leaks.

In still another embodiment of an in-line fluid treatment device in accordance with the principles of the present invention, the retainer is a generally annular ring sized so as to fit over a portion of both the cover and the base so as to hold the cover and the base together.

In another embodiment of an in-line fluid treatment device in accordance with the principles of the present invention, the treatment device further includes a plurality of blades disposed within the treatment chamber, extending radially inward from the rim thereof, for directing fluid flow within the treatment chamber so as to promote efficient fluid treatment.

A variety of additional advantages of the invention will be set forth in part in the description that follows, and in part will be obvious from the description, or may be learned by practice of the invention. The advantages of the invention will be realized and attained by means of the elements and combinations particularly pointed out in the claims. In particular, a fluid treatment device in accordance with the principles of the present invention is suitable for use as an in-line toilet bowl cleaner. However, it is to be understood that both the foregoing general description and the following detailed description are exemplary and explanatory only and are not restrictive of the invention as claimed.

BRIEF DESCRIPTION OF THE DRAWINGS

Like reference numbers generally indicate corresponding elements in the figures.

DETAILED DESCRIPTION OF THE PREFERRED EMBODIMENT

Figure 1:
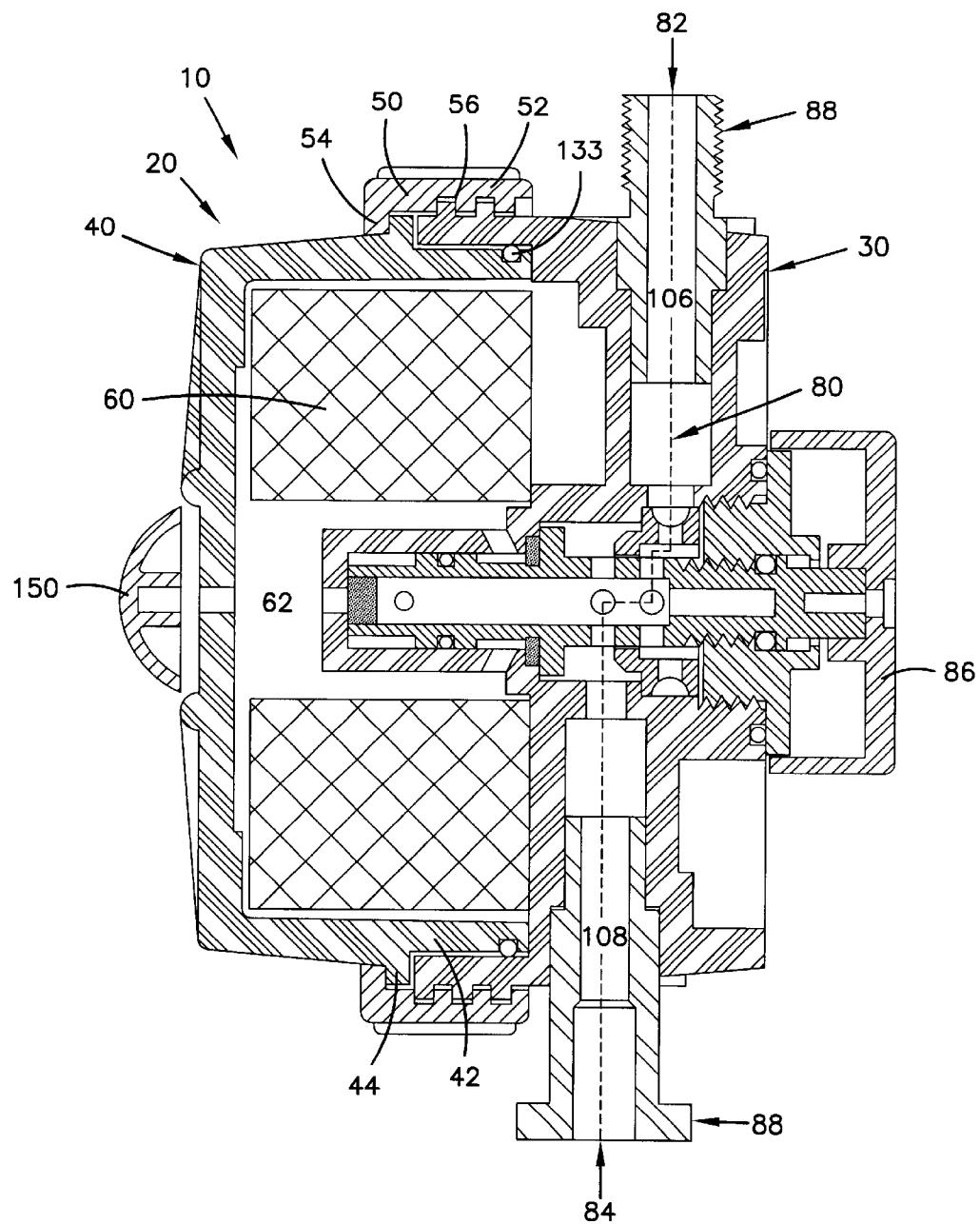
FIG. 1 is a cross-section of an embodiment of an in-line fluid treatment device in accordance with the principles of the present invention, shown in a fully closed position.
Figure 2:
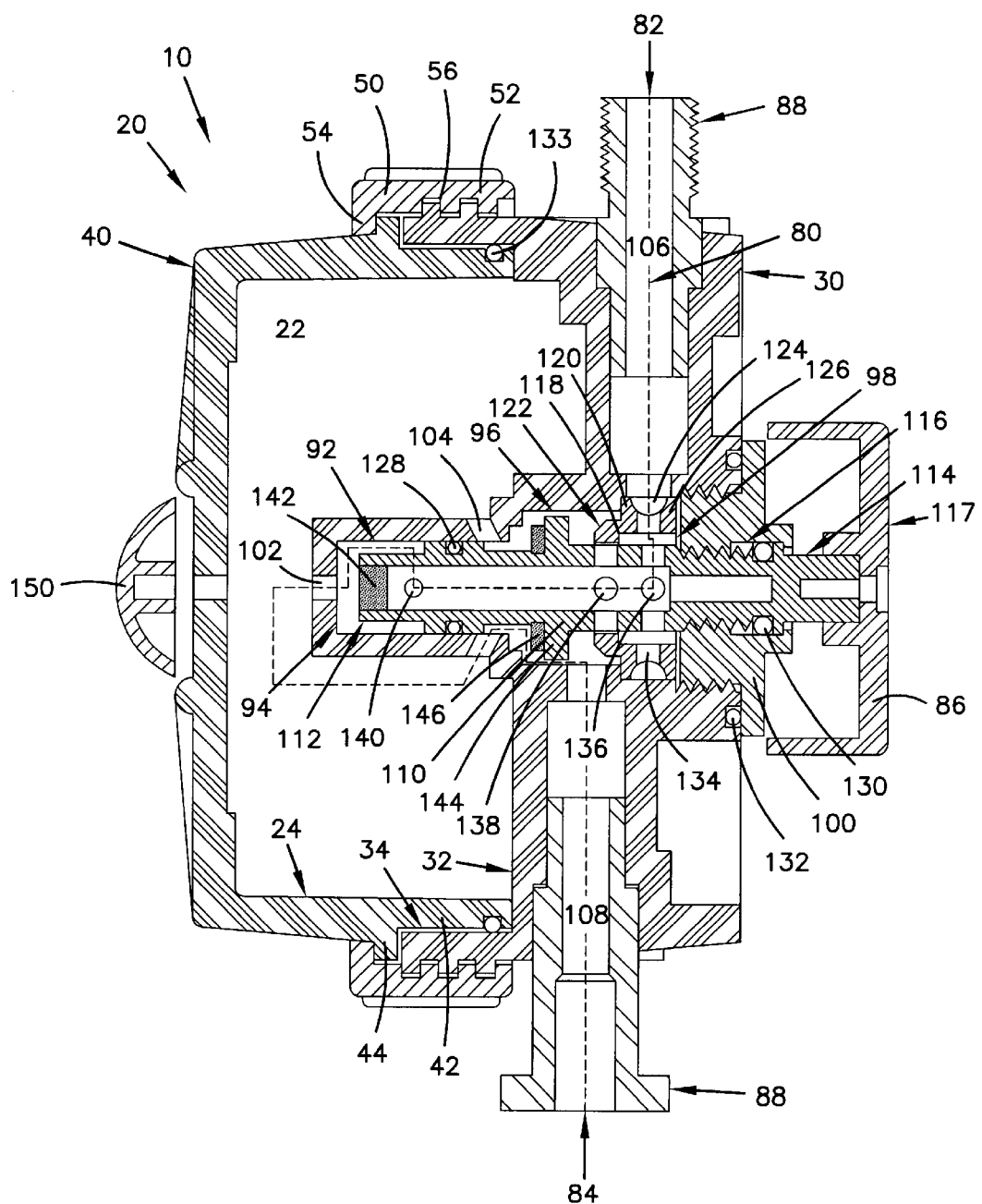
FIG. 2 is a cross-section of the in-line fluid treatment device shown in FIG. 1, shown in a fully open position.
Figure 3:
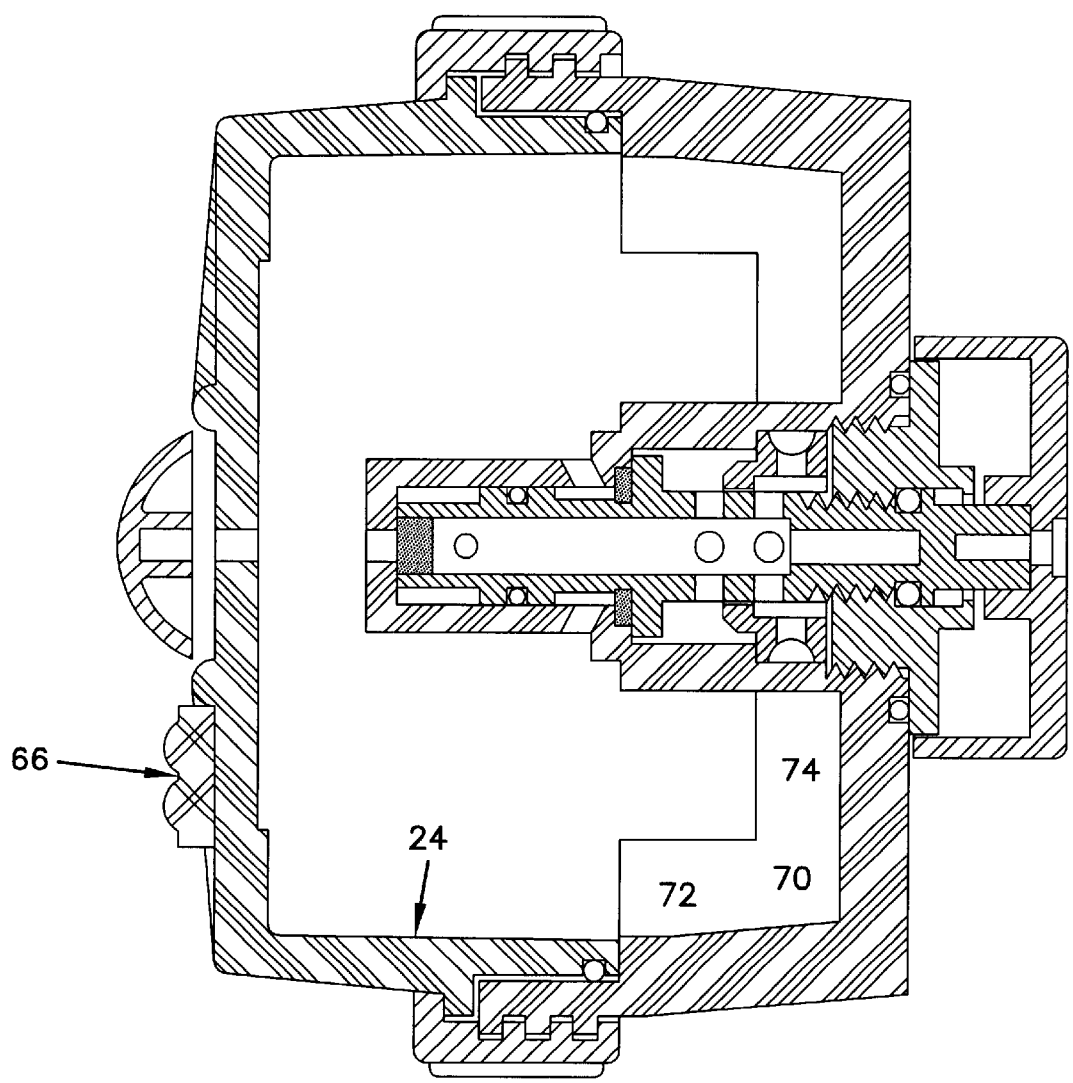
FIG. 3 is a cross-section of the in-line fluid treatment device shown in FIG. 1, the cross-section being rotated 90 from that shown in FIG. 1.
Figure 4:
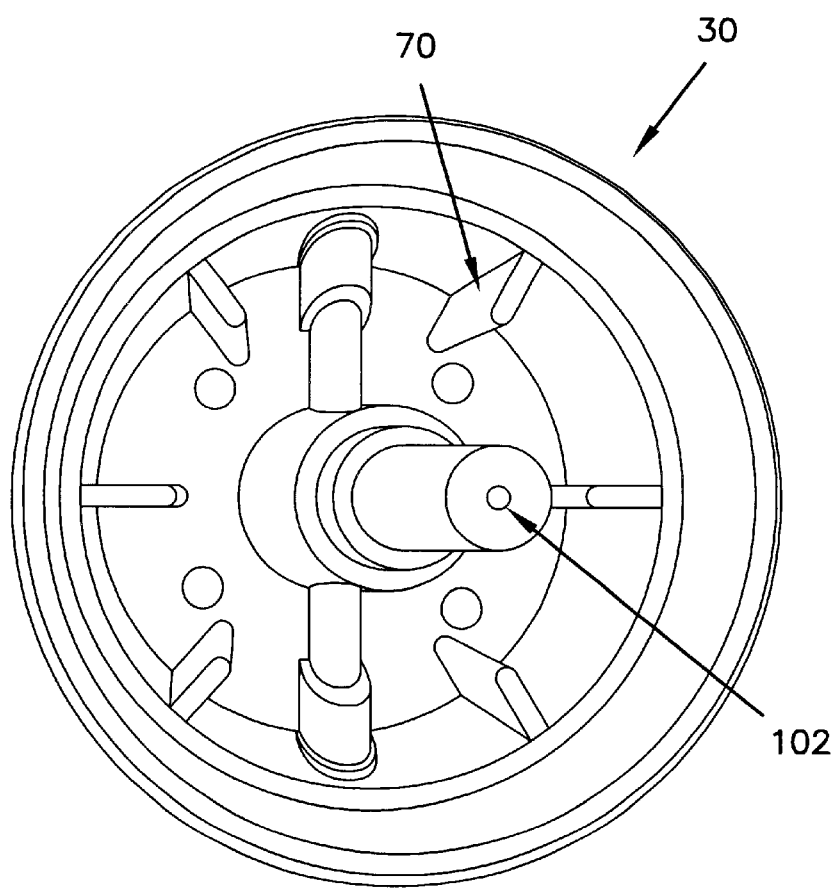
FIG. 4 is a perspective view of the base of an embodiment of an in-line fluid treatment device in accordance with the principles of the present invention, with blades that do not have a first and a second portion.

FIGS. 1–3 illustrate an embodiment of an in-line fluid treatment device in accordance with the principles of the present invention, the treatment device generally being referenced by the reference number 10. The treatment device is suitable for connection with fluid supply 12 (not shown) and fluid exhaust 14 (not shown). It is envisioned that the fluid supply 12 will comprise a tube, such as a hose or pipe.

However, it will be apparent to those knowledgeable in the art that this arrangement is exemplary only, and that other fluid supplies, including but not limited to a pump, reservoir, etc., may be equally suitable. Likewise, it is envisioned that the fluid exhaust 14 will comprise a tube, such as a hose or pipe. However, it will be apparent to those knowledgeable in the art that this arrangement is exemplary only, and that other fluid exhausts, including but not limited to a drain, toilet bowl, etc., may be equally suitable. Fluid supplies and exhausts are well known, and are not further detailed here.

It is furthermore envisioned that the device 10 will be suitable for use with water as a fluid. However, it will be apparent to those knowledgeable in the art that this is exemplary only, and that the device may be equally suitable for use with other fluids.

The fluid treatment device 10 comprises a housing 20, which in turn comprises a base 30 and a cover 40. The cover 40 is suitable for engaging the base 30 to form a fluid-tight seal. The base 30 and cover 40 cooperate to define a treatment chamber 22 within the housing. The treatment device further comprises a retainer 50 for removably retaining the cover 40 on the base 30.

It is envisioned that an embodiment of an in-line fluid treatment device 10 in accordance with the principles of the present invention will be suitable for use with a fluid pressure of at least 500 pounds per square inch as supplied by the fluid supply 12.

It is envisioned that one of the cover 40 and the base 30 comprises a generally annular lip 42. The other of the cover 40 and the base 30 defines a generally circular opening 32. The lip 42 is sized so as to fit within the opening 32, such that the lip 42 and an edge 34 of the opening 32 cooperate to form a generally fluid-tight fit when the base 30 and the cover 40 are engaged. Such a configuration is advantageous, in that when the pressure inside the housing 12 is higher than the pressure outside the housing 12, the pressure differential biases the lip outward, against the edge 34 of the opening 32. Thereby, as pressure increases, any deformation of the housing 12 due to internal overpressure results in a tighter seal, rather than in the formation of leaks in the housing 12. It is envisioned that an o-ring 133 is disposed between the lip 42 and the edge 34, so as to further facilitate a fluid-tight seal. As shown, the lip 42 is disposed on the cover 40, and the opening 32 is defined by the base 30, with the o-ring 133 disposed on the outer surface of the lip 42. However, it will be apparent to those knowledgeable in the art that the o-ring 133 could be located on the inner surface of the edge 34. Likewise, it will be apparent to those knowledgeable in the art that this arrangement is exemplary only, and that it would be equally suitable for the lip 42 to be disposed on the base 30 and the opening 32 to be defined by the cover 40. Furthermore, it will be apparent to those knowledgeable in the art that this configuration is exemplary only, and that other configurations for producing a fluid-tight seal may be equally suitable.

It is envisioned that the cover 40 will comprise a radial outwardly extending flange 44, wherein the diameter of the cover 40 at the flange 44 is greater than the diameter of the cover 40 elsewhere. It is further envisioned that the retainer 50 will comprise a generally annular ring, and that the retainer 50 will comprise first and second portions 52 and 54. The first portion 52 is sized so as to fit over the cover 40 at the flange 44, and furthermore being sized so as to fit over at least a portion of the base 30. The second portion 54 is sized so as to fit over the cover 40 other than at the flange 44, but not so as to fit over the cover 40 at the flange 44. It is further envisioned that at least one of the base 30 and the retainer 50 will comprise a retaining mechanism 56, for retaining the retainer 50 in place. However, it will be apparent to those knowledgeable in the art that this configuration is exemplary only, and that other retainer configurations may be equally suitable.

It is additionally envisioned that the retaining mechanism 56 will comprise screw threads, and will be located both on the base 30 and the retainer 50. However, it will be apparent to those knowledgeable in the art that this configuration is exemplary only, and that other retaining mechanisms, including but not limited to bayonet joints, clamps, etc. may be equally suitable.

As is visible in FIG. 1, the device 10 is adapted to accept a treatment cartridge 60 within the treatment chamber 22, the treatment cartridge 60 being adapted to treat fluid in a desired fashion. It is envisioned that the treatment cartridge 60 will comprise a chemical compound adapted to release a cleaning agent, such as a detergent, into the fluid. However, it will be apparent to those knowledgeable in the art that this is exemplary only, and that other chemical compounds, alone or in combination, and including but not limited to compounds adapted to release coloring agents, antibacterial agents, freshening agents, etc., may be equally suitable. Likewise, chemical compounds adapted to absorb or combine with substances present in the fluid, including but not limited to dissolved minerals or other contaminants from the fluid, may be equally suitable. Furthermore, it will be apparent to those knowledgeable in the art that non-chemical cartridges, including but not limited to mechanical filters, reverse-osmosis devices, etc. may be equally suitable for use as a treatment cartridge 60.

It is envisioned that the treatment cartridge 60 will be generally disc-shaped, and will define at least one aperture 62 therethrough, whereby fluid flow through the treatment cartridge 60 is enabled. However, it will be apparent to those knowledgeable in the art that this configuration is exemplary only, and that other configurations may be equally suitable.

It is further envisioned that the cartridge 60 is removable, whereby another cartridge substituted for it, as at the end of the useful operating life of the cartridge.

As is visible in FIG. 3, it is also envisioned that the device 10 will comprise an indicator 66 to indicate a need to replace the cartridge 60. It is further envisioned that the indicator 66 will be a light emitting diode (LED). However, it will be apparent to those knowledgeable in the art that this is exemplary only, and that other indicators, or no indicator at all, may be equally suitable.

It is envisioned that the device 10 will comprise a plurality of blades 70 disposed within the treatment chamber 22, for directing the flow of fluid within the treatment chamber 22. This is advantageous, in that such blades enable efficient fluid treatment. In a preferred embodiment, it is envisioned that the blades 70 extend radially inward from a rim 24 of the treatment chamber 22. It is further envisioned that the blades 70 comprise a first portion 72 and a second portion 74, wherein the second portion 74 is further from the rim 24 of the treatment chamber 22 than the first portion 72, and wherein the second portion 74 is of lesser height than the first portion 72. It is additionally envisioned that the device 10 will comprise six blades 70, spaced evenly around the rim 24 of the treatment chamber 74. This configuration has been determined to produce favorable fluid flow characteristics within the treatment chamber 22. However, it will be apparent to those knowledgeable in the art that this configuration is exemplary only, and that other configurations of blades, in particular blades of generally uniform height, or no blades at all, may be equally suitable, depending on factors including but not limited to the particular fluid to be treated.

It is also envisioned that the device 10 comprises a pressure release valve 150 to release pressure in the housing 12. This is advantageous, in that if there is an overpressure inside the housing 12, it may deform the housing 12 to the point that it is difficult or impossible to disengage the cover 40 from the base 30. Furthermore, if there is a substantial overpressure inside the housing 12, removal of the cover 40 from the base 30 without first releasing the pressure could prove hazardous. Pressure release valves are well known, and are not further detailed herein.

With regard to the internal fluid flow structure, this application references U.S. Pat. No. 5,404,594, incorporated above by reference, and in particular FIGS. 2–6, as illustrating in detail a valve structurally and functionally similar to the exemplary valve described below.

As shown in FIGS. 1–2, it is envisioned that the in-line fluid treatment device 10 comprises an in-line conduit 80 that define a path for the flow of fluid through the housing 20 from an inlet port 82 to an outlet port 84. An adjusting knob 86 is mounted onto the housing 20. The inlet port 82 is suitable for connection to the fluid supply 12, and the outlet port 84 is likewise suitable for connection to a fluid exhaust 14. Various attachment apparatus and/or mounting mechanisms 88, such as screw threads, flanges, bolts, nuts, and washers, might be used to connect the inlet port 82 to the fluid supply 12, and likewise might be used to connect the outlet port 84 to the fluid exhaust 14. Suitable attachment means are well known, and are not further detailed herein. Fluid from the fluid supply 12 is delivered to the fluid exhaust 14 through the device 10.

FIGS. 1–2 show cross-sectional views of an in-line fluid treatment device 10 in accordance with the principles of the present invention along an axis that reveals the internal valve structure. There is shown an axial bore 90 defined by the housing 20. The axial bore 90 has a smaller diameter section 92 at a first end 94 and a larger diameter section 96 at a second end 98. A hollow screw 100 is partially threadedly received in the larger diameter section 96 at the second end 98. A first opening 102 proximate the first end 94 provides fluid communication between the axial bore 90 and the treatment chamber 22. A plurality of second openings 104 further from the first end 94 than the first opening 102 also provide fluid communication between the axial bore 90 and the treatment chamber 22.

An inlet passageway 106 conducts fluid from the inlet port 82 into the axial bore 90. An outlet passageway 108 conducts fluid from the axial bore 90 to the outlet port 84.

The axial bore 90 receives a hollow valve member 110. A first end 112 of the valve member 110 is disposed within first end 94 of the axial bore 90, whereas the second end 114 of the valve member 110 is disposed within a bore 116 in the hollow screw 100 and fixedly connects to the adjusting knob 86. The hollow valve member 110 is threadedly mounted in the bore 116 of the hollow screw 100 for reciprocal movement thereof upon movement of the knob 86. Since the hollow valve member 110 can be moved relative to the screw 100, the relative position of the hollow valve member 100 in the axial bore 90 is adjusted by turning the knob 86.

It is envisioned that the adjusting knob 86 is suitably marked with a scale on a surface 117 of the knob 86 showing different positions of the hollow valve member 110 in the axial bore 90. In particular there is a marking indicating when the device 10 is turned off such that none of the fluid flowing through the device 10 is treated by the treatment cartridge 60 in the treatment chamber 22. Various positions might then be marked or scaled with numbers indicating the portion of the fluid flowing through the device 10 that is treated by the treatment cartridge 60 in the treatment chamber 22. However, it will be apparent to those knowledgeable in the art that this configuration is exemplary only, and that other configurations of marking scales or no marking scale at all may be equally suitable.

It is envisioned that a sleeve member 118 is fixedly mounted into the large diameter section 96 of the axial bore 90 adjacent to the hollow screw 100 so as to be stationary relative to the hollow screw 100. A front portion 120 of the sleeve member 118 has a tapered outer surface 122. The hollow valve member 110 is slidably mounted relative to the sleeve member 118. Thus, the relative position between the hollow valve member 110 and the sleeve member 118 is adjusted by the knob 86. The outer diameter of the hollow valve member 110 and the inner diameter of the front portion 120 of the sleeve member 118 abut each other so that the fluid under pressure is blocked by the front portion 120. A middle portion 124, integral with the front portion 120 and a back portion 126, has a spool-shaped outer surface wherein the outer diameter of the middle portion 124 is smaller than that of the front and back portions 121, 127. The inner diameter of the middle and back portions 124, 126 is larger than the outer diameter of the hollow valve member 110. Thus, a circular gap is disposed between the hollow valve member 110 and the middle and back portions 124, 126 so that fluid is free to flow therebetween.

The plurality of second openings 104 extend from the treatment chamber 22 to the axial bore 90, so as to carry fluid from the treatment chamber 22 to the axial bore 90. An o-ring 128 is disposed about the hollow valve member 110 in the smaller diameter section 92 of the axial bore 90 between the first opening 102 and the plurality of second openings 104. The o-ring 128 is designed to fill in the space between the inside wall of the smaller diameter section 92 and the outside surface of the hollow valve member 110 so that fluid exiting the treatment chamber 22 through the plurality of second openings 104 is not allowed to flow back to the treatment chamber 22 through the first opening 102.

An o-ring 130 is disposed proximate the second end 114 of the hollow valve member 110 so as to provide a fluid-tight seal between the hollow valve member 110 and the hollow screw 100. An o-ring 132 is disposed around the hollow screw 100 so as to provide a fluid-tight seal between the hollow screw and the base 30 of the housing 20.

As shown in FIGS. 1–2, the middle portion 124 of the seal member 118 defines a first plurality of orifices 134 (not all orifices in the set are shown for purposes of illustration). In addition, valve member 110 defines second, third, and fourth pluralities of orifices 136, 138, and 140 (not all orifices in each set are shown for purposes of illustration). In addition, the first end 112 of the hollow valve member 110 is sealed by a seal member 142. The valve member 110 also comprises a circular member 144 which projects from the outer surface of the hollow valve member 110 between the third and fourth plurality of orifices 138 and 140, and a washer 146 adjacent the circular member 144 in the direction of the fourth plurality of orifices 140.

As shown in FIGS. 1–2, the middle portion 124 is aligned to the inlet passageway 106 so that fluid from the inlet port flows into the middle portion 124 of the sleeve member 118 through the first plurality of orifices 134. The fluid then flows into the hollow valve member 110 through the second plurality of orifices 136.

As is visible in FIG. 1, when the device 10 is in a fully closed position, that is, when substantially none of the fluid passing through the device 10 is treated in the treatment chamber 22, the valve member 110 is at maximum insertion into the housing 20. Since the fourth plurality of orifices 140 is at a downstream position compared to the third plurality of orifices 138, and since in the fully closed position the first opening 102 is sealed by a seal member 142, substantially all of the fluid from the inlet passageway 106 flows through the third plurality of orifices 138 into the larger diameter section 96 of the axial bore 90, as opposed to flowing to the fourth plurality of orifices 140 at the first end 112 of the hollow valve member 110. Because the circular member 144 and washer 146 obstruct the flow of fluid from the larger diameter section 96 to the plurality of second openings 104, the fluid then flows from the larger diameter section 96 to the outlet passageway 108. Substantially none of the fluid passes through the treatment chamber 22.

As is visible in FIG. 2, when the device 10 is in a fully open position, that is, when substantially all of the fluid passing through the device 10 is treated in the treatment chamber 22, the valve member 110 is at minimum insertion into the housing 20. Since the third plurality of orifices 138 is obstructed by the sleeve member 118, substantially all of the fluid flows through the fourth plurality of orifices 140, and through the first opening 102 into the treatment chamber 22. There the fluid is treated by the treatment cartridge 60. The fluid then exits the treatment chamber through the plurality of second openings 104, moving into the larger diameter section 96 of the axial bore 90. The fluid then flows from the larger diameter section 96 to the outlet passageway 108. Substantially all of the fluid passes through the treatment chamber 22.

It will be apparent that the device 10 may also be in a partially open position, wherein a portion of the fluid passing through the device 10 passes through the treatment chamber 22, and a portion does not. The portion of fluid flowing through the treatment chamber depends on how much of the third plurality of orifices 136 is obstructed by the sleeve member 118, which depends on the relative position of the hollow valve member 110, the position of which in turn is adjustable by manipulation of the adjusting knob 86. The operation of the in-line fluid treatment device 10 is thus easily controlled by the user.

Parts of the in-line fluid treatment device 10 can be made of various materials, such as metal, plastic or polymer, etc.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A fluid treatment device adapted to be connected to a fluid supply and a fluid exhaust, the device comprising:
    a housing, said housing comprising a base and a cover suitably engagable with said base to form a fluid-tight fit, said base and said cover cooperating to define a treatment chamber within said housing, said treatment chamber being adapted to accept a treatment cartridge for treating fluid in said treatment chamber;
    a retainer adjusted to removably retain said cover on said base;
    an in-line conduit configured to conduct fluid from the fluid supply to said treatment chamber and thence to the fluid exhaust, and to conduct fluid from the fluid supply to the fluid exhaust without passing through said treatment chamber;
    a valve disposed to control the flow of fluid through the in-line conduit;
    an adjustment mechanism configured so as to adjust said valve to control a portion of fluid flowing from the fluid supply that flows to said treatment chamber;
    wherein one of said base and said cover comprises a generally annular lip, and the other of said base and said cover defines a generally circular opening, said lip being sized so as to fit within said opening, whereby said lip and said opening cooperate to form a generally fluid-tight fit when said base and said cover are engaged, and whereby said lip is biased against an edge of said opening when a pressure inside said treatment chamber is greater than a pressure outside said treatment chamber.

2. The fluid treatment device of claim 1, wherein said fluid treatment device is suitable for use with a fluid pressure from the fluid supply of at least 500 pounds per square inch.

3. The fluid treatment device of claim 1, wherein said cover has a radial outwardly extending flange, wherein a diameter of said cover is greater at said flange than a diameter of said cover other than at said flange.

4. The fluid treatment device of claim 3, wherein said retainer comprises a generally annular ring, said ring having first and second portions, said first portion being sized so as to fit over said cover at said flange, said second portion being sized so as to fit over said cover other than at said flange, said first portion further being sized so as to fit over at least a portion of said base when said base and said cover are engaged.

5. The fluid treatment device of claim 4, wherein at least one of said retainer and said base comprise a retaining mechanism for retaining said retainer to said base.

6. The fluid treatment device of claim 1, further comprising a plurality of blades disposed within said treatment chamber for directing the fluid flow, said blades extending radially inward from a rim of said treatment chamber.

7. The fluid treatment device of claim 6, wherein said plurality of blades extend radially inward from a rim of said treatment chamber.

8. The fluid treatment device of claim 7, wherein said plurality of blades include first and second blade portions, said second blade portion being further from said rim of said treatment chamber than said first blade portion, said second blade portion being of lesser height than said first blade portion.

9. The fluid treatment device of claim 7, wherein said plurality of blades comprises six blades evenly spaced about said rim of said treatment chamber.

10. The fluid treatment device of claim 1, further comprising a treatment cartridge.

11. The fluid treatment device of claim 10, wherein said cartridge comprises a chemical cleaning agent.

12. The fluid treatment device of claim 10, wherein said cartridge comprises a cleaning filter.

13. The fluid treatment device of claim 10, where in said cartridge is replaceable.

14. The fluid treatment device of claim 13, wherein said housing comprises an indicator for indicating that said cartridge is in need of replacement.

15. The fluid treatment device of claim 1, further comprising a pressure release valve, whereby pressure in said treatment chamber may be released.

16. A fluid treatment device adapted to be connected to a fluid supply and a fluid exhaust, the device comprising:

a housing, said housing comprising a base and a cover suitably engagable with said base to form a fluid-tight fit, said base and said cover cooperating to define a treatment chamber within said housing, said treatment chamber being adapted to accept a treatment cartridge for treating fluid in said treatment chamber;

a retainer adjusted to removably retain said cover on said base;

an in-line conduit configured to conduct fluid from the fluid supply to said treatment chamber and thence to the fluid exhaust, and to conduct fluid from the fluid supply to the fluid exhaust without passing through said treatment chamber;

a valve disposed to control the flow of fluid through the in-line conduit;

an adjustment mechanism configured so as to adjust said valve to control a portion of fluid flowing from the fluid supply that flows to said treatment chamber;

wherein said in-line conduit comprises:

an axial bore, wherein a hollow sleeve member of said valve is fixedly received;

an inlet passageway configured to conduct fluid from the fluid supply into said hollow sleeve member and thence into a hollow valve member of said valve through a first plurality of orifices of said hollow sleeve member and a second plurality of orifices of said hollow valve member, said hollow sleeve member being disposed along said hollow valve member;

an outlet passageway extending from said hollow valve member through a third plurality of orifices of said hollow valve member, said outlet passageway being configured to conduct fluid to the fluid exhaust;

said hollow valve member further including a fourth plurality of orifices; and a passageway, disposed between said first end of said in-line conduit and said axial bore, configured to fluidly connect said fluid treatment chamber with said axial bore.

17. The fluid treatment device of claim 16, wherein said adjustment mechanism adjusts said relative position between said hollow sleeve member and said third plurality of orifices of said hollow valve member so as to adjust a volume of fluid directly flowing to said fluid passageway, wherein when said third plurality of orifices are entirely open, all fluid is conducted directly from the fluid supply to said outlet passageway, when said third plurality of orifices are partially closed, some fluid is conducted directly from the fluid supply to said outlet passageway and some fluid is conducted from the fluid supply to said treatment chamber to said outlet passageway, and when said third plurality of orifices are entirely closed to said outlet passageway, all fluid is conducted from the fluid supply through said treatment chamber to said outlet passageway.

18. The fluid treatment device of claim 17, wherein said hollow sleeve member includes a front portion which covers said third plurality of orifices when said third plurality of orifices are entirely closed to said outlet passageway, a middle portion on which said first plurality of orifices are disposed, and a back portion, said middle and back portions being in fluid communication with said second plurality of orifices so as to enable fluid from the fluid supply to flow into said hollow valve member.

19. A method for in-line fluid treatment, the method comprising:

connecting a fluid treatment device to a fluid supply and a fluid exhaust, whereby all fluid from said fluid supply flows through said fluid treatment device and thence to said fluid exhaust, the fluid treatment device comprising:

a housing, said housing comprising a base and a cover suitably engagable with said base to form a fluid tight fit, said base and said cover cooperating to define a treatment chamber within said housing;

a retainer adjusted to removably retain said cover on said base;

a treatment cartridge disposed within said treatment chamber, said cartridge being adapted to treat fluid in said treatment chamber;

an in-line conduit configured to conduct fluid from the fluid supply to said treatment chamber and thence to the fluid exhaust, and to conduct fluid from the fluid supply to the fluid exhaust without passing through said treatment chamber;

a valve disposed to control the flow of fluid through the in-line conduit;

an adjustment mechanism configured so as to adjust said valve to control a portion of fluid flowing from the fluid supply that flows to said treatment chamber;

wherein one of said base and said cover comprises a generally annular lip, and the other of said base and said cover defines a generally circular opening, said lip being sized so as to fit within said opening, whereby said lip and said opening cooperate to form a generally fluid-tight fit when said base and said cover are engaged, and whereby said lip is biased against an edge of said opening when a pressure inside said treatment chamber is greater than a pressure outside said treatment chamber.

20. A method for in-line fluid treatment, the method comprising:

connecting a fluid treatment device to a fluid supply and a fluid exhaust, whereby all fluid from said fluid supply flows through said fluid treatment device and thence to said fluid exhaust, the fluid treatment device comprising:

a housing, said housing comprising a base and a cover suitably engagable with said base to form a fluid tight fit, said base and said cover cooperating to define a treatment chamber within said housing;

a retainer adjusted to removably retain said cover on said base;

a treatment cartridge disposed within said treatment chamber, said cartridge being adapted to treat fluid in said treatment chamber;

an in-line conduit configured to conduct fluid from the fluid supply to said treatment chamber and thence to the fluid exhaust, and to conduct fluid from the fluid supply to the fluid exhaust without passing through said treatment chamber;

a valve disposed to control the flow of fluid through the in-line conduit;

an adjustment mechanism configured so as to adjust said valve to control a portion of fluid flowing from the fluid supply that flows to said treatment chamber;

wherein said in-line conduit comprises:

an axial bore, wherein a hollow sleeve member of said valve is fixedly received;

an inlet passageway configured to conduct fluid from the fluid supply into said hollow sleeve member and thence into a hollow valve member of said valve through a first plurality of orifices of said hollow sleeve member and a second plurality of orifices of said hollow valve member, said hollow sleeve member being disposed along said hollow valve member;

an outlet passageway extending from said hollow valve member through a third plurality of orifices of said hollow valve member, said outlet passageway being configured to conduct fluid to the fluid exhaust;

said hollow valve member further including a fourth plurality of orifices; and a passageway, disposed between said first end of said in-line conduit and said axial bore, configured to fluidly connect said fluid treatment chamber with said axial bore.

* * * * *